United States Patent [19]

Rosencwaig et al.

[11] 4,129,385
[45] Dec. 12, 1978

[54] PHOTOACOUSTIC SAMPLE CELL

[75] Inventors: Allan Rosencwaig, Elyria; Robert J. Emary, Wakeman, both of Ohio

[73] Assignee: Gilford Instrument Laboratories, Oberlin, Ohio

[21] Appl. No.: 772,728

[22] Filed: Feb. 28, 1977

[51] Int. Cl.$^2$ ............................................. G01N 21/24
[52] U.S. Cl. ..................................... 356/244; 356/432
[58] Field of Search ................................ 356/201, 244; 250/358 R; 73/67.2

[56] References Cited

U.S. PATENT DOCUMENTS

| 3,948,345 | 4/1976 | Rosencwaig | 73/67.2 |
| 4,028,932 | 6/1977 | Rosencwaig | 73/67.2 |

OTHER PUBLICATIONS

McClelland et al., "Photoacoustic Spectroscopy With Condensed Samples," *Applied Optics,* vol. 15, No. 11, Nov. 1976, pp. 2658-2662.

*Primary Examiner*—John K. Corbin
*Assistant Examiner*—R. A. Rosenberger
*Attorney, Agent, or Firm*—Baldwin, Egan, Walling & Fetzer

[57] ABSTRACT

A photoacoustic cell for analyzing solid and quasi-solid samples and which includes a table for holding a sample to be analyzed and which is movably disposed in the cell housing and positioned in a sample test position to form a part of the cell chamber in which the sample is to be analyzed or tested. The cell chamber is formed having a window through which a light source may pass onto the sample whereby energy is released inside said cell chamber characteristic of the light source and is sufficient to provide a signal characteristic of the absorbance of the sample and which is sensed by a microphone in said chamber. At the completion of the sample test, the table may be moved to a sample load/unload position for discharge of the tested sample and preparatory to having a subsequent sample placed thereon for analysis.

7 Claims, 2 Drawing Figures

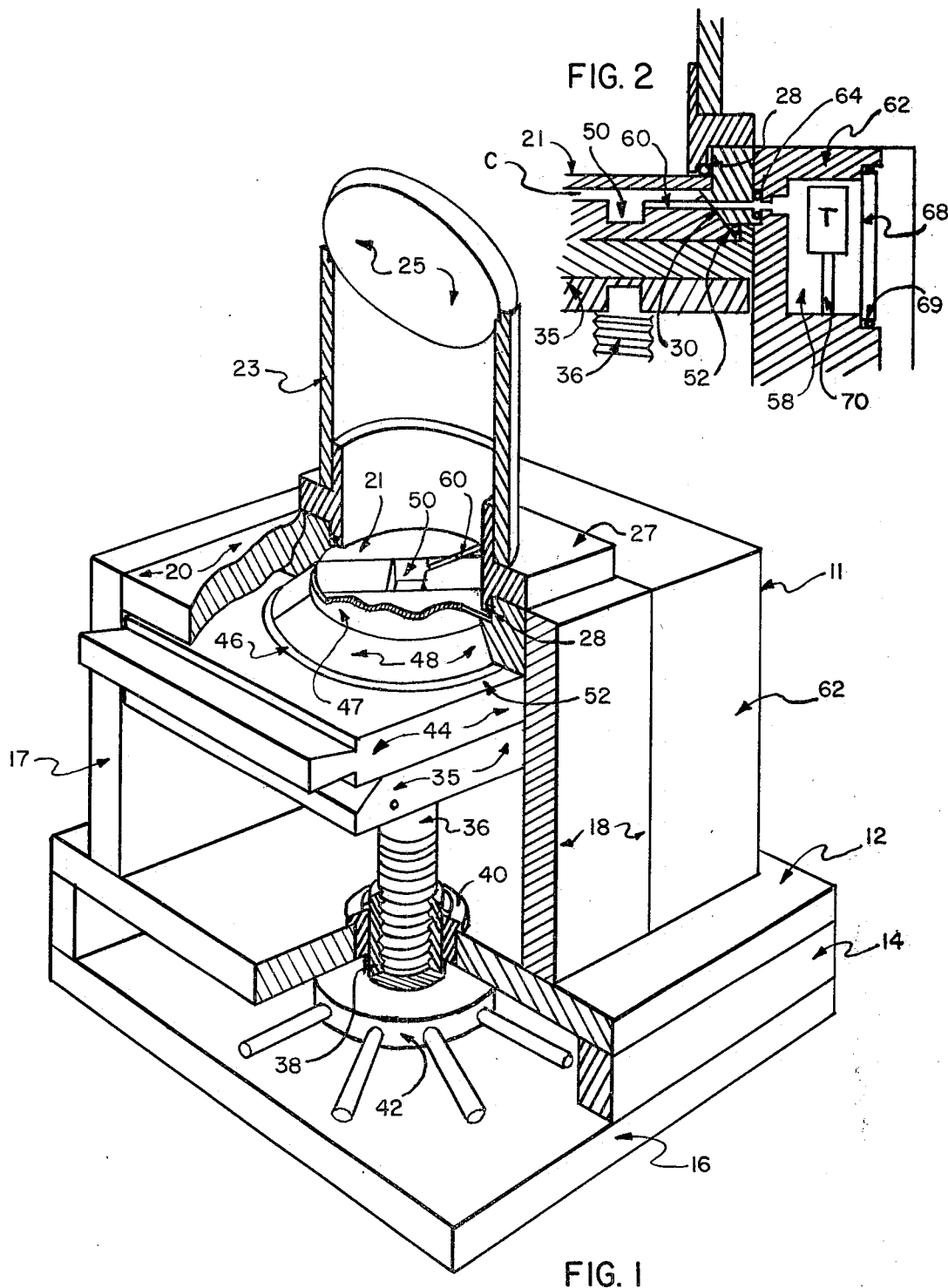

PHOTOACOUSTIC SAMPLE CELL

FIELD OF THE INVENTION

This invention relates to photoacoustic cells and, particularly, to photoacoustic cells for analyzing solid or quasi-solid samples.

BACKGROUND OF THE INVENTION

An article appeared on page 510, Volume 11, of the Philosophical Magazine in 1881 in which Alexander Graham Bell reported upon certain experiments which he conducted to study the sound-emitting properties of materials when exposed to the action of rapidly interrupted sunlight. Bell, among other things, introduced samples of material into a chamber and passed an intermittent beam of sunlight therein to produce audible effects. Bell observed that when the sample was in an acoustical resonant chamber the maximum response was achieved at a frequency of interruption equivalent to the resonant frequency of the chamber. While Bell was primarily interested in producing sound, he did recognize that this effect could be employed to study the properties of the material.

In the U.S. Pat. No. 3,948,345 which issued on Apr. 6, 1976, there is disclosed methods and means for analyzing solid and quasi-solid substances. This is accomplished by detecting signals which are established between a substance being tested and a surrounding fluid by a source of radiant energy whose amplitude is varied and whose frequency is scanned. An acoustic responsive transducer is located to sense the changes in the energy level of the surrounding fluid and transduces these acoustical energy changes into electrical signals that are characteristic of the substance being analyzed.

In the aforesaid U.S. patent there is disclosed in FIGS. 9–21 thereof the types of response graphs or curves obtained for a plurality of solid substances when analyzed by said patented system and method. Further reference to said patent is directed to obtain a more thorough understanding of said photoacoustic system for analyzing solid and quasi-solid substances.

Reference is also directed to the copending application, Ser. No. 567,640, filed Apr. 14, 1975 which is a continuation-in-part of U.S. Pat. No. 3,948,345, and which application discloses several embodiments of photoacoustic cells especially designed for use in said photoacoustic system of said U.S. Pat. No. 3,948,345.

The photoacoustic cell of this application is especially designed for use with the system and method of analysis of solid and quasi-solid materials as described in said aforesaid U.S. Pat. No. 3,948,345 and enables series of tests to be easily repetitively performed, said cell being relatively simple in structure and operation as compared to other sample test cells heretofore known.

Therefore, an object of this invention is to provide a new and improved photoacoustic cell.

Another object of this invention is to provide a new and improved photoacoustic cell which is readily adaptable to perform repetitive tests on solid and quasi-solid substances.

Another object of this invention is to provide a new and improved photoacoustic cell which is applicable for a wide variety of uses.

Other objects and advantages of the photoacoustic cell of this invention will become apparent to one skilled in the art upon reference to the following disclosure of a preferred embodiment.

BRIEF DESCRIPTION OF THE INVENTION

The photoacoustic cell of this invention includes a housing having a sample test chamber, one part of which chamber is defined by a table upon which the sample to be tested is disposed. The table is adjustably movable between a sample load/unload position whereat the sample to be tested is deposited thereon and a sample test position at which the table is moved in the housing to define a part of the wall of the test chamber with the sample thereon located within said chamber.

A source of pulsating or chopped light is passed into the chamber whereat it impinges upon and is absorbed by the test sample. The energy level of the sample is thus elevated and gives off energy in the form of heat at the same rate of pulsation of the light source.

The energy released by the test sample similarly activates the fluid (i.e. air or other suitable liquid) in the test chamber thus providing resultant pressure variation of said chamber fluid which is sensed by a suitable pressure responsive tranducer capable of generating an audible signal representative of said pressure variations.

The sample chamber has a predetermined volume with the sample in place; in its present embodiment being in the range of 0.05–10 cubic centimeters. Also, the linear distance between the top of the sample and the chamber window, later described, is within the range of 0.5–2.5 millimeters.

The housing includes a conduit or tunnel connecting the sample chamber to the pressure-responsive transducer. The minimum lateral dimension of this conduit should be not less than 0.5 milimeters to minimize the effect of thermoviscous damping. Reference is also directed to the aforementioned CIP operation for additional dimensional relationships.

Reference is also directed to the following two papers for additional dimensional relations: Photoacoustic Effect with Solids: A Theoretical Treatment, by Allan Rosencwaig and Allen Gersho, Science: Nov. 7, 1975; Vol. 190. Theory of the Photoacoustic Effect with Solids, by Allan Rosencwaig and Allen Gersho, Journal of Applied Physics, Jan. 1976.

It has been found that good results are obtained when the volume of the sample chamber and the tunnel are substantially equal, although other volume relationships therebetween may also be contemplated herein.

DESCRIPTION OF THE DRAWINGS

FIG. 1 is a perspective view, shown partly in section, of the photoacoustic sample test cell of this invention; and FIG. 2 is a partial sectional view of the test cell to more particularly show the structural relationship between the test chamber, connecting tunnel and pressure-responsive transducer.

DETAILED DESCRIPTION OF THE INVENTION

Referring to FIG. 1, the photoacoustic sample cell of this invention is identified at 10 and includes a housing 11 that is box-like in configuration and mounted on platform 12 which, in turn, is supported on side rails 14 attached to and extending upwardly from opposed sides of a flat base member 16.

In the embodiment illustrated herein, the platform 12, rails 14 and base member 16 are preferably formed of metal so as to provide adequate mass to prevent vibration to the sample under test.

As best seen in FIG. 1, the housing 11 is formed by side wall members 17 and 18 extending perpendicularly upwardly from the platform 12. A top wall 20 is interposed between the uppermost edge of said side walls, and is provided with a transparent circular window 21 formed of material that is transparent of the spectral region of interest and through which light energy may be introduced into the housing test chamber.

A tubular mirror holder 23 is mounted over the window 21 and has a suitable mirror 25 angularly disposed as for example at an angle of 45° and thus positioned to direct a beam of light energy from a suitable source (not shown) down the tubular holder 23 and thence through the window 21 into the test or sample chamber identified at C in FIG. 2.

As seen in FIG. 1, the top wall 20 is centrally formed with an aperture defined by a circular seat 26 upon which is disposed the circular window 21. Busing 27 is suitably secured within the aperture to hold the window 21 in place and an O-ring 28, or the like, is interposed between the bushing wall and said window to provide a fluid seal therebetween.

The mirror holder 23 is mounted upright on the bushing 27 to thus position mirror 25 directly over the window 21 and underlying sample chamber C.

As seen in FIGS. 1 and 2, the aperture in the top wall 20 is formed to provide an annular, downwardly and outwardly projecting wall 30 conical in configuration which begins at the inner edge of the circular seat 26 and projects downwardly and outwardly to the underside of the top wall.

This conical wall 30 and the underface of the window 21 define the fixed part of the sample chamber C.

A table 35 is disposed in the housing 11 and is centrally mounted on the upper end of threaded shaft 36, said shaft being threadedly journalled in internally threaded bushing 38 rotatably carried within bearing 40 mounted centrally in platform 12.

A capstan 42 disposed in the housing 11 below the platform 12 is securely fastened to the underside of bushing 38 whereupon rotation of the same threadedly moves the shaft 36 correspondingly upwardly or downwardly to result in raising or lowering the table 35 relative to the housing top wall 20.

As seen in FIG. 1, the housing 11 is open on its one side to permit the samples of material to be introduced into the sample chamber C for analysis.

For this purpose a tray 44 is placed upon the upper surface of the table 35, and is formed with an upwardly projecting conical-shaped platform 46 having a circular flat top wall 47 bounded by an outwardly and downwardly extending wall 48, frustoconical in configuration.

The platform 46 is formed centrally with a removable, rectangular insert with a pocket 50 located centrally therein in whereby the sample is to be deposited and to position the sample directly within the beam of light passing through the window 21.

With this configuration, the solid or quasi-solid sample is placed within the cavity or pocket 50 and the tray 44 is then placed on the table 35. The capstan 42 is rotated to raise the table 35 upwardly in the housing 11 to the position as shown whereat the conical wall 48 of the tray platform 46 sealingly engages the conical wall 30 in the top wall 20, and O-ring 52, interposed between the tray 44 and the underside of the top wall 20, provides a fluid seal between said tray 44, platform 46 and the housing top wall 20.

The parts of the housing and sample tray forming the sample chamber C are preferably found of polished aluminum or stainless steel.

The table 35, tray 44 and platform 46 are illustrated in their raised, sample test position whereat the platform 46 defines the lower part of the sample chamber C. As aforesaid, the volume of this chamber C may be in the range of 0.05–10 cubic centimeters for good results.

With this construction, a deposit of loose particles such as powders may be deposited in a horizontal plane and permits the formation of the photoacoustic sample cell with a minimum of disturbance to the sample. Further, no additional tools or other accessories are required to form the sample cell whereby mechanical positioning and chamber sealing integrity are assured.

With the sample to be tested thus disposed in the sample cavity 50 and a source of light, as for example the chopped light source described in my U.S. Pat. No. 3,948,345, passing through lens 25 and window 21 sufficiently to be absorbed by said sample, the resultant pulsating energy given off by said sample causes a corresponding pulsation to the entrapped chamber fluid.

This fluid pulsation is then transmitted to a transducer T located in transducer chamber 58 whereat said pulsation is transposed by said transducer T into a representative electrical signal corresponding to the absorbance characteristics of said sample.

For this purpose, a tunnel or conduit 60 is formed in the top wall 20 of the housing 11 opening at its inner end to the sample chamber C and at its opposite end to the transducer chamber 58 formed in the housing back wall 62. As seen in FIG. 2, suitable O-ring seal 64 is used between the back wall 62 and top wall 20 to maintain an integral fluid seal at the juncture of tunnel 60 and transducer chamber 58.

The access opening 66 of chamber 58 as seen in FIG. 2 may also be provided with a suitable closure plate 68 and peripheral O-ring seal 69 to ensure a fluid seal of the sample chamber C, tunnel 60 and transducer chamber 58 from atmosphere.

Good transmission of the pulsating energy signals is obtained when the volume of the tunnel 60 is approximately equal with respect to the volume of test chamber C.

The pulsating energy signals impinge upon the transducer T and the resultant electrical signals are then passed by conductors 70 to appropriate signal responsive apparatus whereat a characteristic response curve may be made of the material being tested. As aforementioned such response curve may be like those disclosed in FIGS. 9–21 in U.S. Pat. No. 3,948,345.

What is claimed is:

1. A sample cell for photoacoustic measurement of a solid and quasi-solid sample material in a fluid medium comprising a table and means on said table for receiving a predetermined quantity of sample material thereon, a housing into which the table is selectively inserted in a horizontal plane as to prevent physical disturbance thereto, means for moving said table vertically in said housing between a sample load position and sample test position, said sample receiving means being engageable with said housing when said table is moved to its sample test position to define therebetween a sample test chamber, positioning means interacting between said table and said housing to precisely position the sample material in said test chamber, said sample cell being formed of sufficient mass to enable the sample material to be insensitive to physical vibration, radiant energy deflecting means carried on said housing over said test chamber being operable to direct radiant energy into said chamber effective to correspondingly change the energy level of said sample material and result in like changes in the resident fluid in said chamber.

2. A sample cell as is defined in claim 1 and wherein the sample receiving means is moved into fluid-tight relation with said housing when said table is moved to its sample test position.

3. A sample cell as is defined in claim 1 and wherein tunnel means are formed in said housing and communicating with said sample test chamber.

4. A sample cell as is defined in claim 1 and wherein transducer means are disposed in said housing and exposed to fluid pressure changes of the chamber fluid.

5. A sample cell as is defined in claim 1 and wherein the sample receiving means includes tray means adapted to be movable into and out of said housing and placeable onto the table, and said tray means having wall means movable into a fluid-tight seal with said housing to define the sample test chamber.

6. A sample cell as is defined in claim 1 and wherein means connectable with the table is adjustably movable to move said table to the sample test position and the sample load position.

7. A sample cell as is defined in claim 6 and wherein the means connectable with the table includes a threaded shaft, a capstan connectable with said shaft and rotatable to adjustably rotate said shaft and move said table in said housing.

* * * * *